US008052711B2

(12) United States Patent
Hanse et al.

(10) Patent No.: US 8,052,711 B2
(45) Date of Patent: Nov. 8, 2011

(54) METHOD AND APPARATUS FOR FIXATING AN IMPLANTABLE MEDICAL DEVICE

(75) Inventors: Gary H. Hanse, Ham Lake, MN (US); Matthew A. Bergan, Brooklyn Park, MN (US); Terese A. Bartlett, Harris, MN (US); Ryan T. Bauer, Brooklyn Park, MN (US); Vicki L. Bjorklund, Maple Grove, MN (US); Richard D. Sandstrom, Scandia, MN (US)

(73) Assignee: Medtronic, Inc., Minneapolis, MN (US)

( * ) Notice: Subject to any disclaimer, the term of this patent is extended or adjusted under 35 U.S.C. 154(b) by 1181 days.

(21) Appl. No.: 10/792,413

(22) Filed: Mar. 3, 2004

(65) Prior Publication Data

US 2004/0176782 A1    Sep. 9, 2004

Related U.S. Application Data

(63) Continuation-in-part of application No. 10/115,302, filed on Apr. 3, 2002, now abandoned.

(51) Int. Cl.
*A61M 29/00*    (2006.01)

(52) U.S. Cl. ....................................................... 606/198

(58) Field of Classification Search .................. 606/194, 606/198, 200; 604/104–109
See application file for complete search history.

(56) References Cited

U.S. PATENT DOCUMENTS

| | | | |
|---|---|---|---|
| 3,397,699 A | 8/1968 | Kohl | |
| 3,692,029 A | 9/1972 | Adair | |
| 4,419,819 A | 12/1983 | Dickhudt et al. | |
| 4,519,403 A | 5/1985 | Dickhudt | |
| 4,590,949 A | 5/1986 | Pohndorf | |
| 4,660,571 A | 4/1987 | Hess et al. | |
| 4,664,120 A | 5/1987 | Hess | |
| 4,699,147 A | 10/1987 | Chilson et al. | |
| 4,781,682 A | 11/1988 | Patel | |
| 4,796,643 A | 1/1989 | Nakazawa et al. | |
| 4,913,164 A | 4/1990 | Greene et al. | |
| 4,957,118 A | 9/1990 | Erlebacher | |
| 4,995,868 A | 2/1991 | Brazier | |
| 5,047,045 A * | 9/1991 | Arney et al. ................. 606/194 |
| 5,156,151 A | 10/1992 | Imran | |
| 5,188,602 A | 2/1993 | Nichols | |
| 5,203,773 A | 4/1993 | Green | |
| 5,228,442 A | 7/1993 | Imran | |
| 5,238,007 A | 8/1993 | Giele et al. | |
| 5,239,999 A | 8/1993 | Imran | |
| 5,267,994 A * | 12/1993 | Gentelia et al. ................ 606/15 |
| 5,324,284 A | 6/1994 | Imran | |
| 5,344,439 A * | 9/1994 | Otten ........................... 607/126 |
| 5,397,339 A | 3/1995 | Desai | |
| 5,423,772 A * | 6/1995 | Lurie et al. .................... 604/525 |

(Continued)

FOREIGN PATENT DOCUMENTS

DE    33 00 050    7/1984

(Continued)

*Primary Examiner* — Ryan Severson
(74) *Attorney, Agent, or Firm* — Reed A. Duthler; Stephen W. Bauer

(57) ABSTRACT

A fixation mechanism coupled to an implantable device body extends from a proximal portion of the body to a distal portion of the body and includes a fixation element and a push tube segment. A push tube segment of the mechanism extends proximally from the fixation mechanism to the proximal portion of the body and is adapted to deploy the mechanism.

13 Claims, 15 Drawing Sheets

U.S. PATENT DOCUMENTS

| | | | |
|---|---|---|---|
| 5,462,545 A | 10/1995 | Wang et al. | |
| 5,683,445 A * | 11/1997 | Swoyer | 607/125 |
| 5,702,438 A | 12/1997 | Avitall | |
| 5,707,362 A | 1/1998 | Yoon | |
| 5,855,565 A * | 1/1999 | Bar-Cohen et al. | 604/104 |
| 5,857,999 A | 1/1999 | Quick et al. | |
| 5,876,399 A | 3/1999 | Chia et al. | |
| 5,951,597 A | 9/1999 | Westlund et al. | |
| 6,064,905 A | 5/2000 | Webster, Jr. et al. | |
| 6,231,524 B1 | 5/2001 | Wallace et al. | |
| 6,425,909 B1 | 7/2002 | Dieck et al. | |
| 6,442,435 B2 | 8/2002 | King et al. | |
| 6,498,943 B2 | 12/2002 | Steglich | |
| 6,512,940 B1 | 1/2003 | Brabec et al. | |
| 6,529,779 B1 | 3/2003 | Sutton | |
| 6,574,492 B1 | 6/2003 | Ben-Haim et al. | |
| 6,697,676 B2 | 2/2004 | Dahl et al. | |
| 7,047,084 B2 | 5/2006 | Erickson et al. | |
| 7,110,828 B2 | 9/2006 | Kolberg et al. | |
| 7,330,765 B2 | 2/2008 | Haldeman | |
| 2001/0000800 A1 | 5/2001 | Partridge et al. | |
| 2002/0072787 A1 | 6/2002 | Partridge et al. | |
| 2003/0009130 A1 | 1/2003 | Stecker et al. | |
| 2003/0195603 A1 | 10/2003 | Scheiner et al. | |
| 2003/0199961 A1 | 10/2003 | Bjorklund et al. | |
| 2003/0212361 A1 * | 11/2003 | Boyle et al. | 604/104 |
| 2004/0176782 A1 | 9/2004 | Hanse et al. | |
| 2005/0070981 A1 | 3/2005 | Verma | |
| 2006/0036307 A1 | 2/2006 | Zarembo et al. | |
| 2007/0282412 A1 | 12/2007 | Soltis et al. | |
| 2007/0282414 A1 | 12/2007 | Soltis et al. | |
| 2008/0097567 A1 | 4/2008 | Haldeman | |

FOREIGN PATENT DOCUMENTS

| | | | |
|---|---|---|---|
| EP | 0 546 414 B1 | 4/1997 | |
| EP | 0 779 080 B1 | 5/2003 | |
| WO | WO 03/084433 A2 | 10/2003 | |
| WO | WO 03/084433 A3 | 2/2004 | |
| WO | WO 2007/143303 A2 | 12/2007 | |
| WO | WO 2007/143304 A2 | 12/2007 | |
| WO | WO 2007/143303 A3 | 3/2008 | |
| WO | WO 2007/143304 A3 | 3/2008 | |
| WO | WO 2008/054446 A1 | 5/2008 | |

* cited by examiner

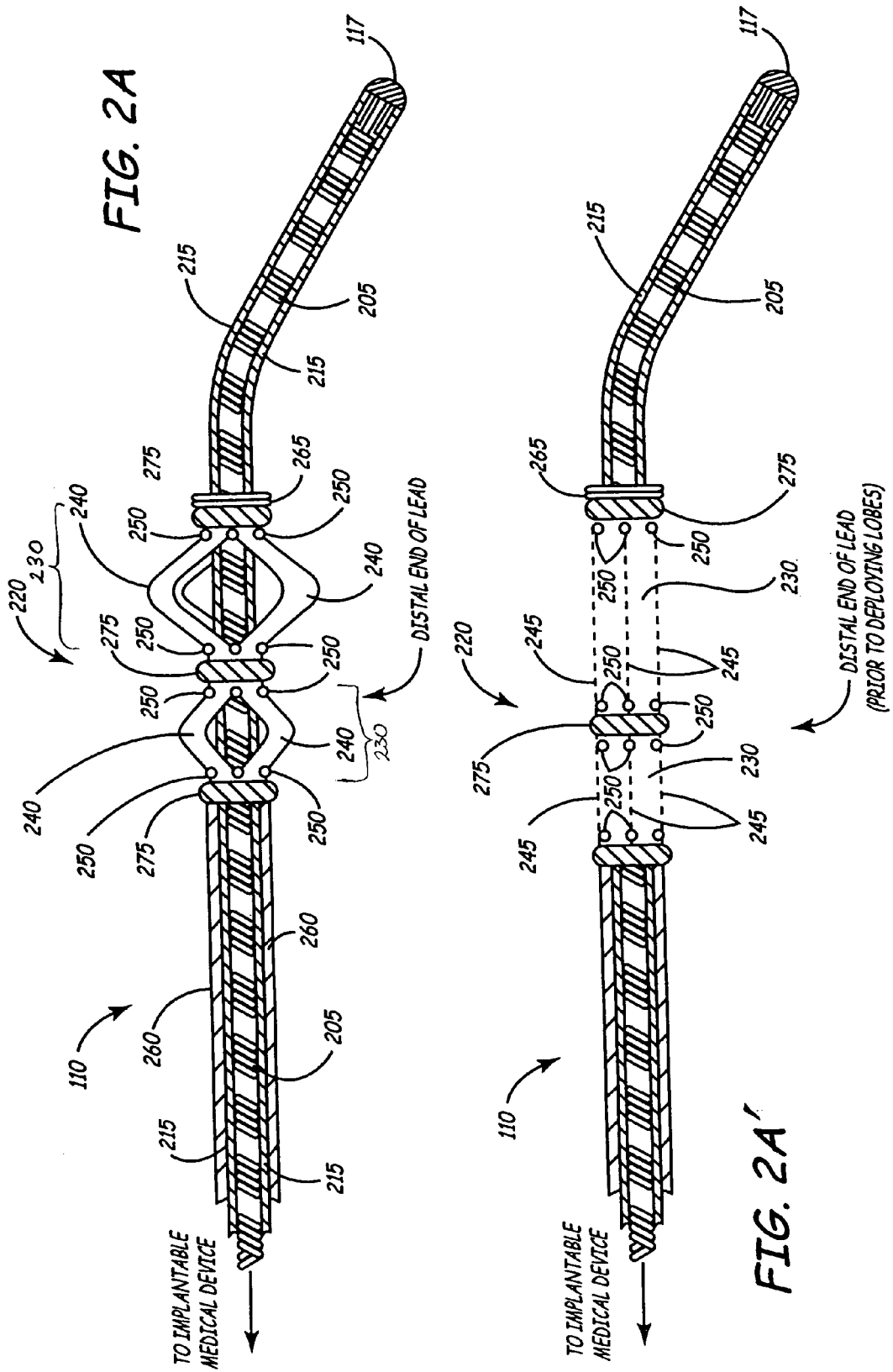

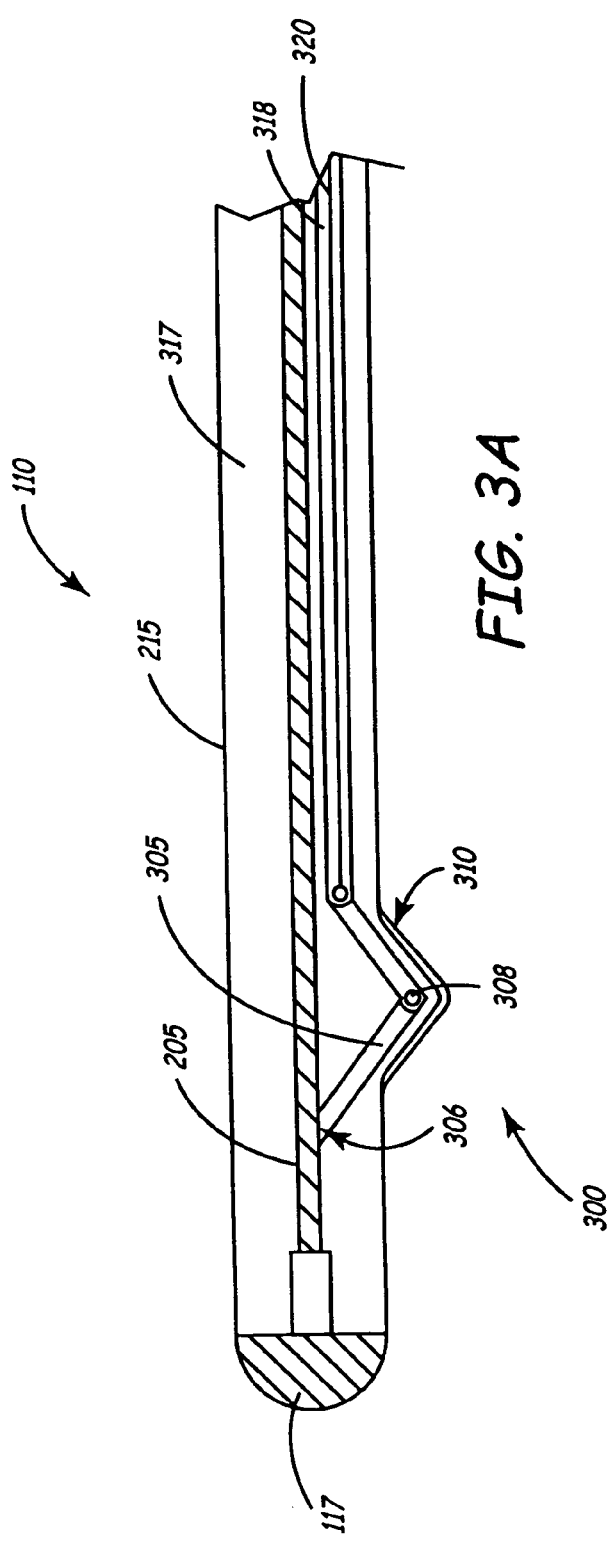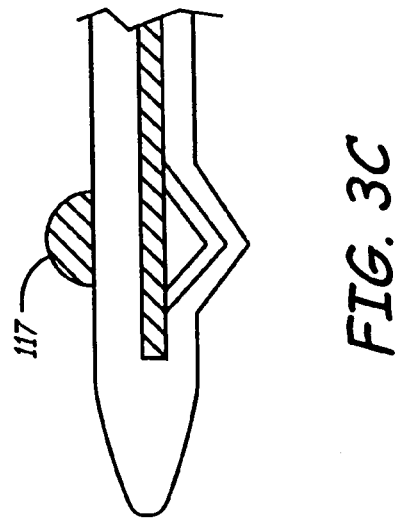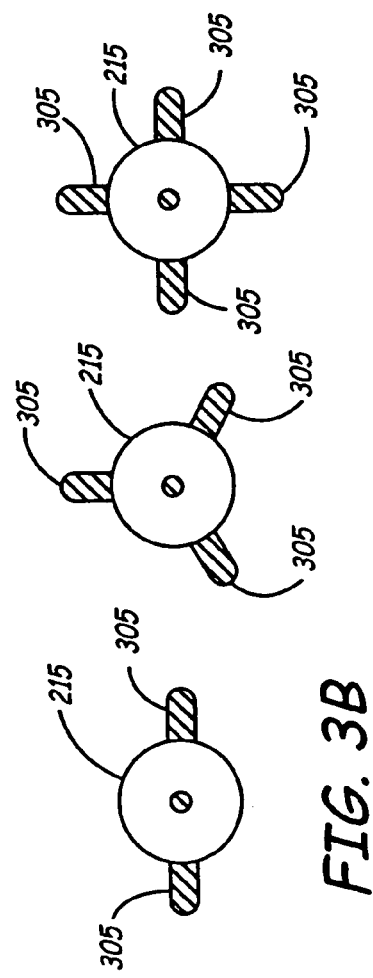

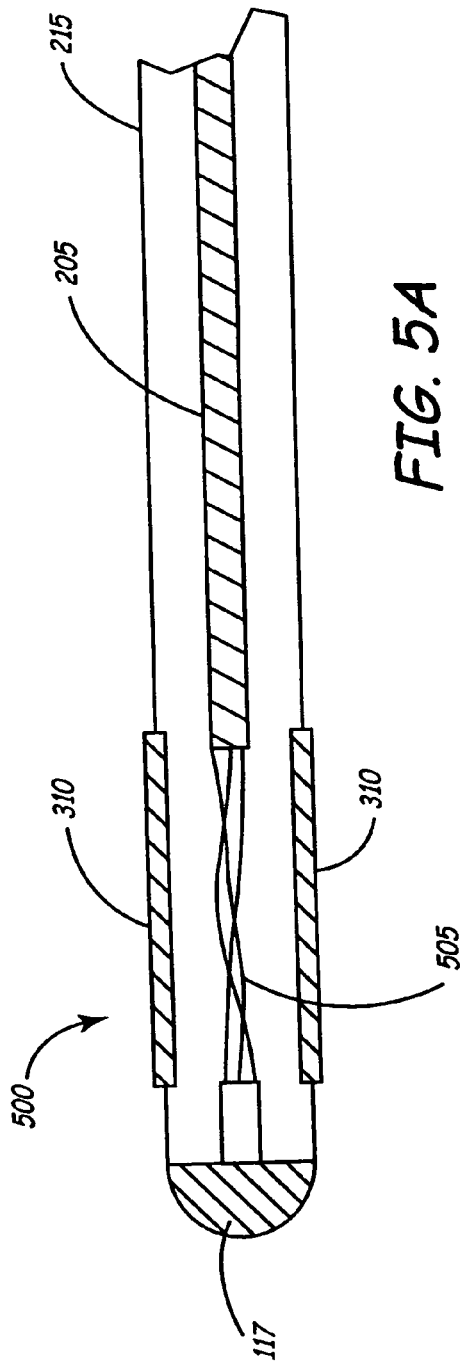
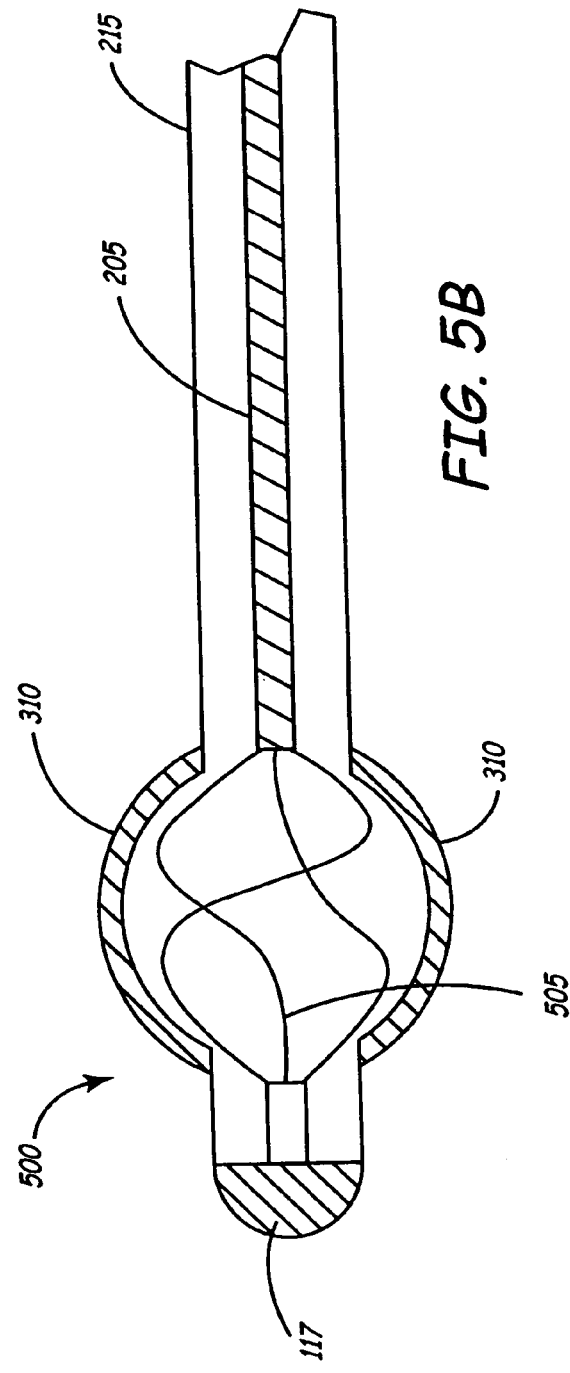

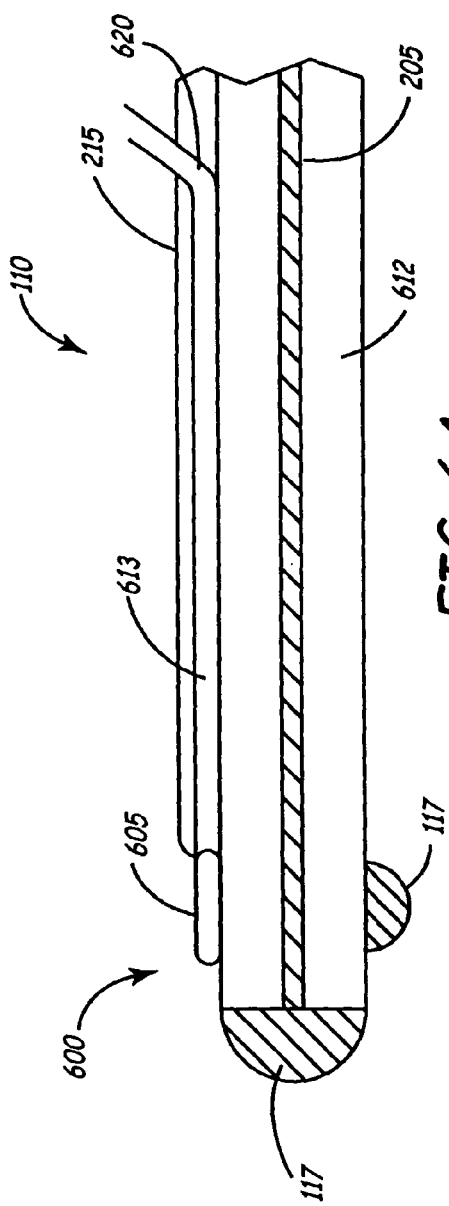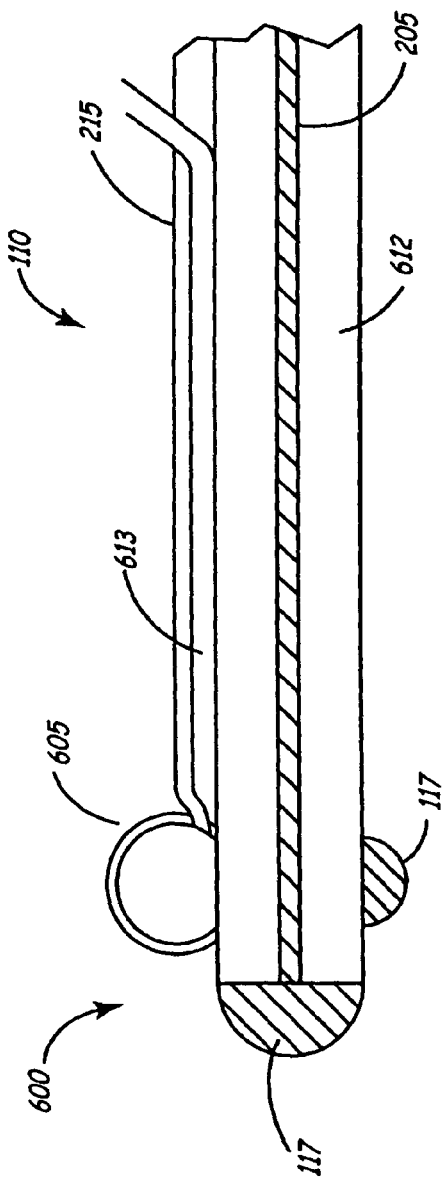

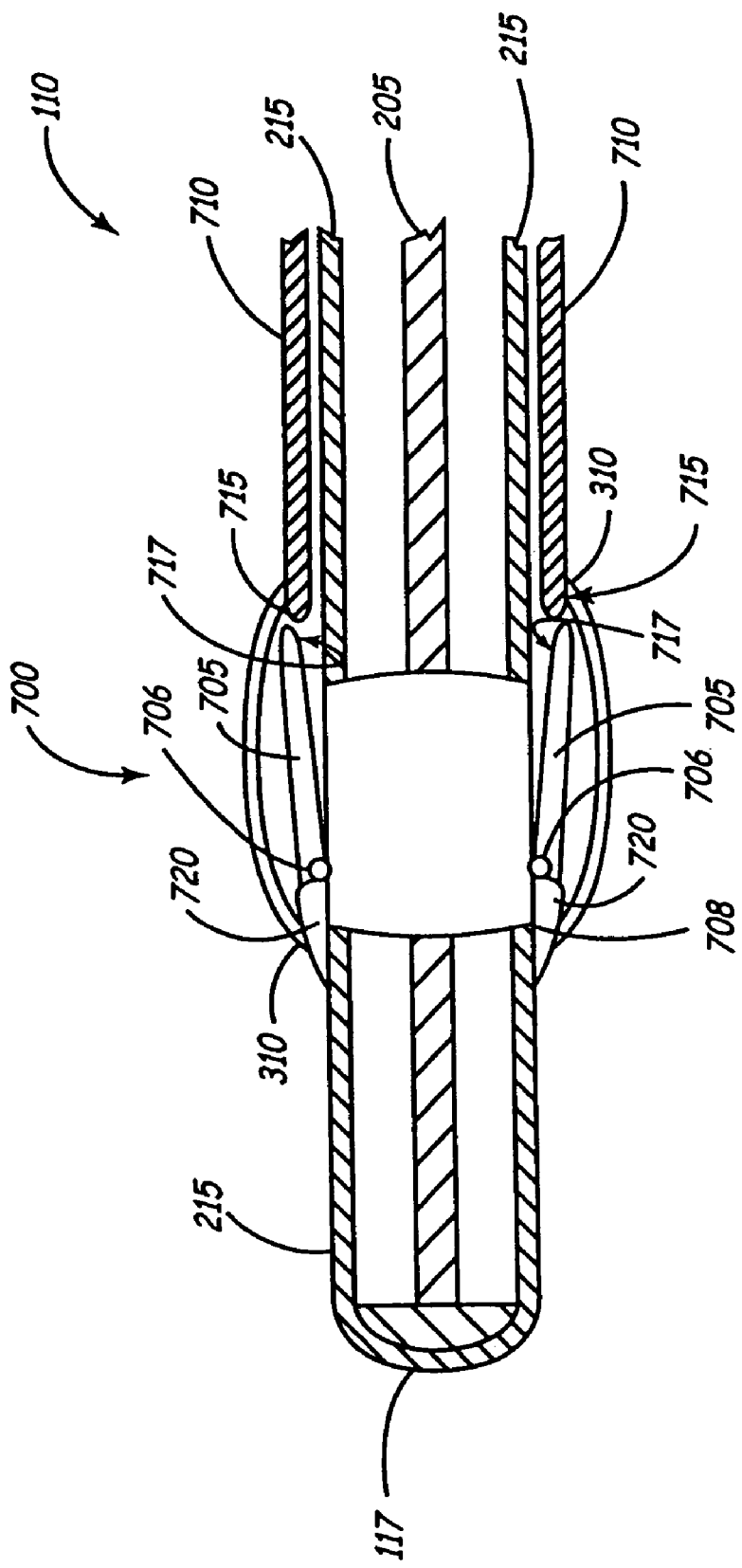

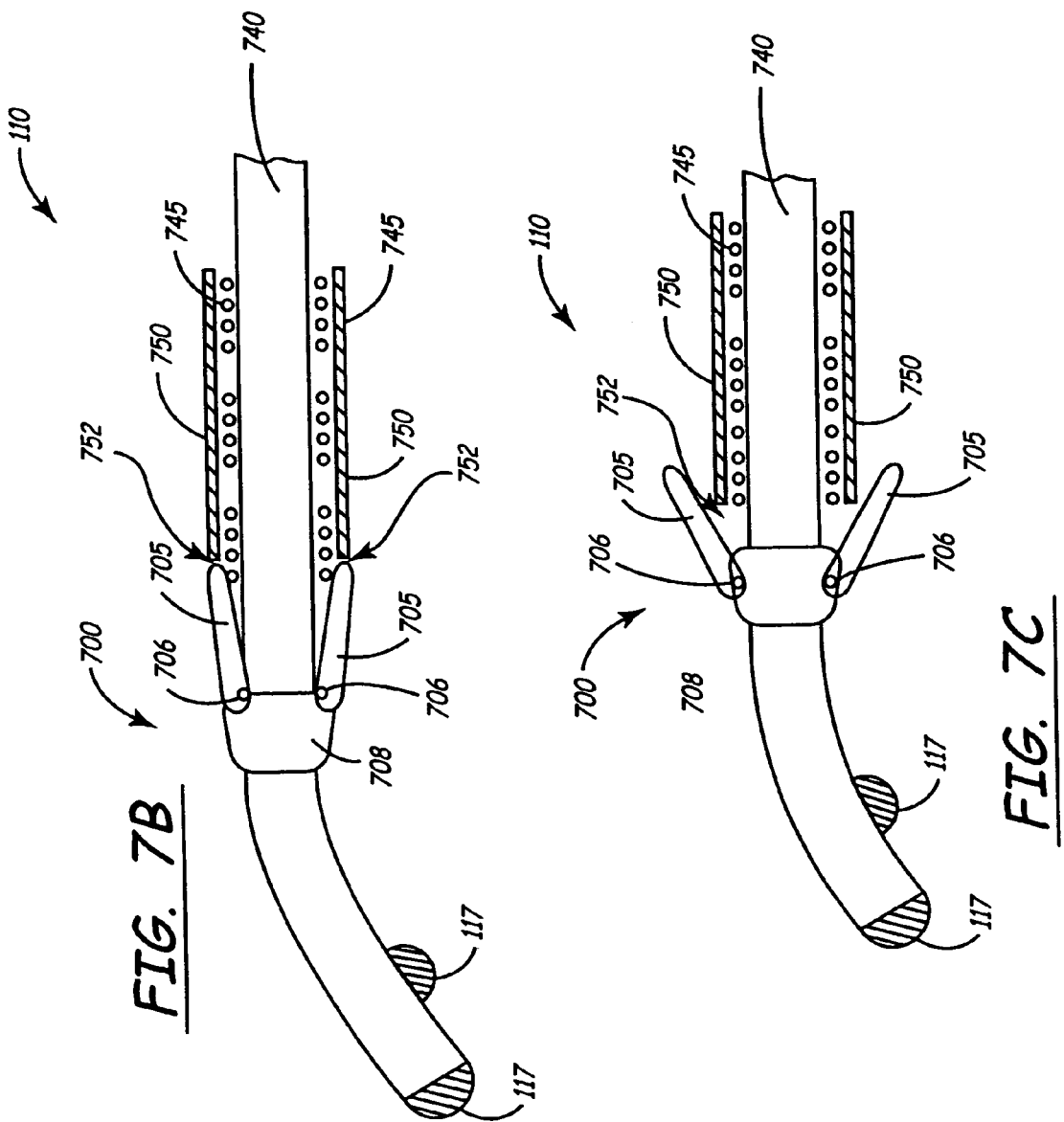

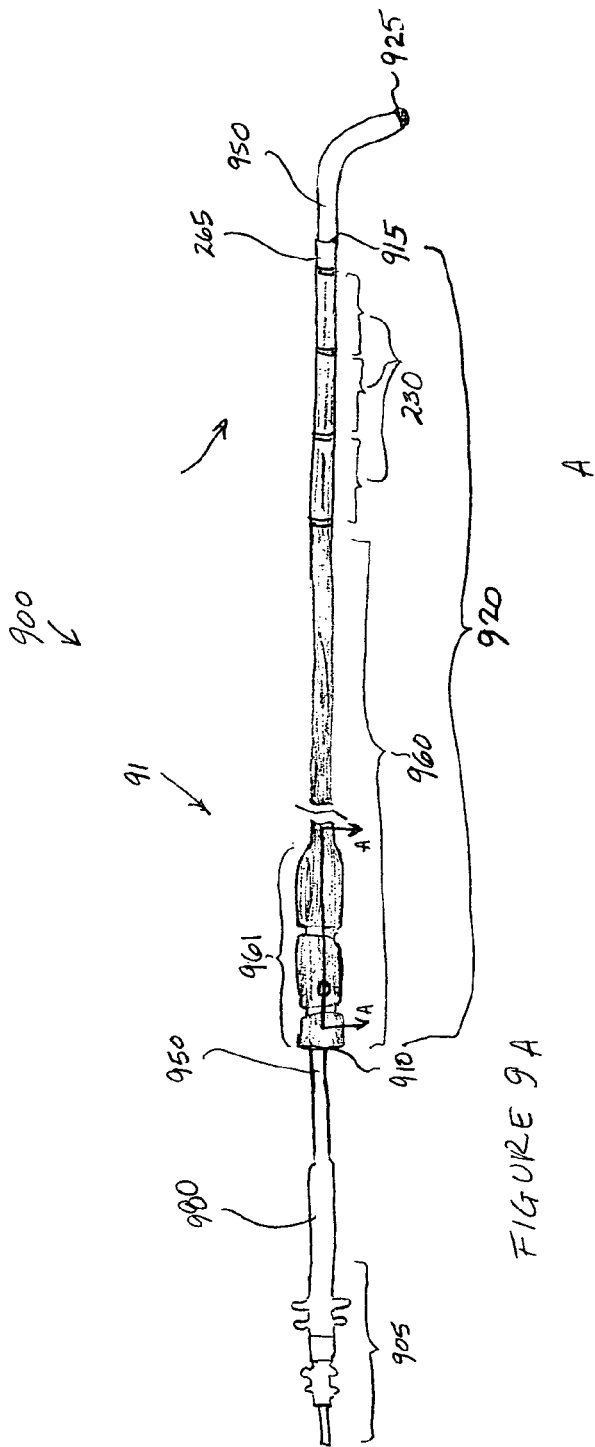
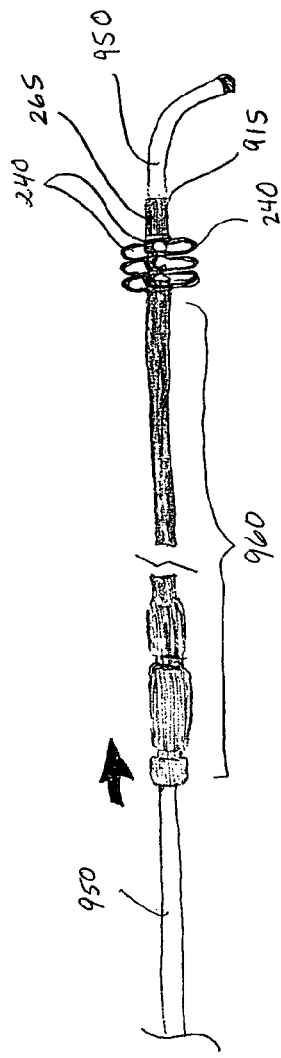
FIGURE 9A
FIGURE 9B

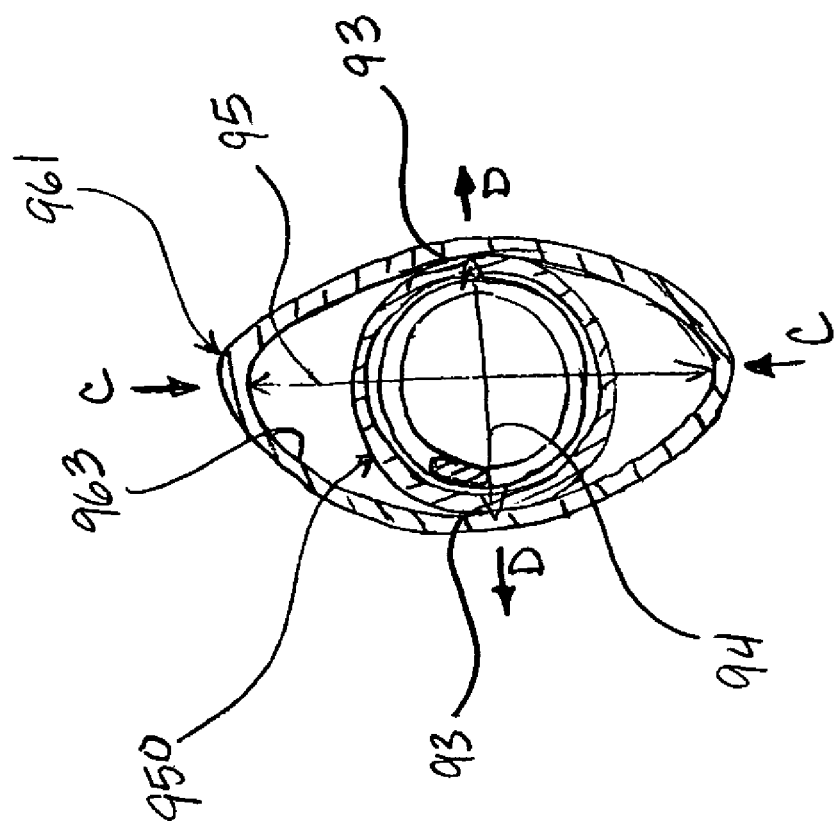

METHOD AND APPARATUS FOR FIXATING AN IMPLANTABLE MEDICAL DEVICE

This Application is a continuation-in-part (CIP) of application Ser. No. 10/115,302 filed Apr. 3, 2002 now abandoned. The entire content of application Ser. No. 10/115,302 is incorporated herein by reference.

FIELD OF THE INVENTION

This invention relates generally to implantable medical devices, and, more particularly, to a fixation mechanism for securing a lead of the implantable medical device within a cardiac vessel of a patient.

DESCRIPTION OF THE RELATED ART

Since their earliest inception some forty years ago, there has been a significant advancement in body-implantable electronic medical devices. Today, these implantable devices include therapeutic and diagnostic devices, such as pacemakers, cardioverters, defibrillators, neural stimulators, drug administering devices, among others for alleviating the adverse effects of various health ailments. Today's implantable medical devices are also vastly more sophisticated and complex than their predecessors, and are therefore capable of performing considerably more complex tasks for reducing the effects of these health ailments.

The implantable medical device is generally implanted within the patient's body and a lead couples the implantable device to a portion of the patient's body, such as the patient's heart, for example. Typically, an electrode is provided at the distal end of the lead, and it is adapted to be disposed at a desired site within a cardiac vessel of the heart, such as a vein. The electrodes typically sense cardiac activity and deliver electrical pacing stimuli (i.e., therapeutic signals) to the patient's heart depending on the sensed cardiac activity.

The pacing leads are commonly implanted within the cardiac vessel with the aid of a stylet that is positioned within a lumen in the lead. If the electrode residing on the distal end of the pacing lead becomes dislodged after implantation within the cardiac vessel, the electrode may not be able to properly sense the cardiac activity of the patient and deliver the electrical pulsing stimuli to the desired area of the patient's heart. If the electrode becomes dislodged from the desired location within the patient's cardiac vessel, a significant amount of time and expense may occur to have the dislodged electrode replanted within the desired site of the cardiac vessel. Moreover, upon dislodgment of the electrode, the patient may be subjected to serious health risks as a result of the electrode not being able to properly sense cardiac activity of the patient and/or deliver a proper therapy to the desired site within the patient's heart.

The present invention is directed to overcoming, or at least reducing the effects of, one or more of the problems set forth above.

BRIEF DESCRIPTION OF THE DRAWINGS

The invention may be understood by reference to the following description taken in conjunction with the accompanying drawings, in which the leftmost significant digit(s) in the reference numerals denote(s) the first figure in which the respective reference numerals appear, and in which:

FIGS. 3A-C show perspective views of the distal portion of the lead having a deployable lobe for fixating the lead to the vessel in accordance with another embodiment of the present invention;

FIGS. 5A-B show a side view perspective of the distal portion of the lead employing a stent for fixating the lead to the vessel in accordance with another embodiment of the present invention;

FIGS. 6A-B show a side view perspective of the distal portion of the lead employing a balloon for fixating the lead to the vessel in accordance with another embodiment of the present invention;

FIGS. 7A-C show a side view perspective of the distal portion of the lead employing a pair of flanges for fixating the lead to the vessel in accordance with another embodiment of the present invention;

FIG. 9A is a plan view of a lead including a fixation mechanism according one embodiment of the present invention;

FIG. 9B is a perspective view of a distal portion of the lead shown in FIG. 9A wherein the fixation mechanism is deployed;

FIG. 10B is a radial section view of an alternate embodiment;

Figure 1:
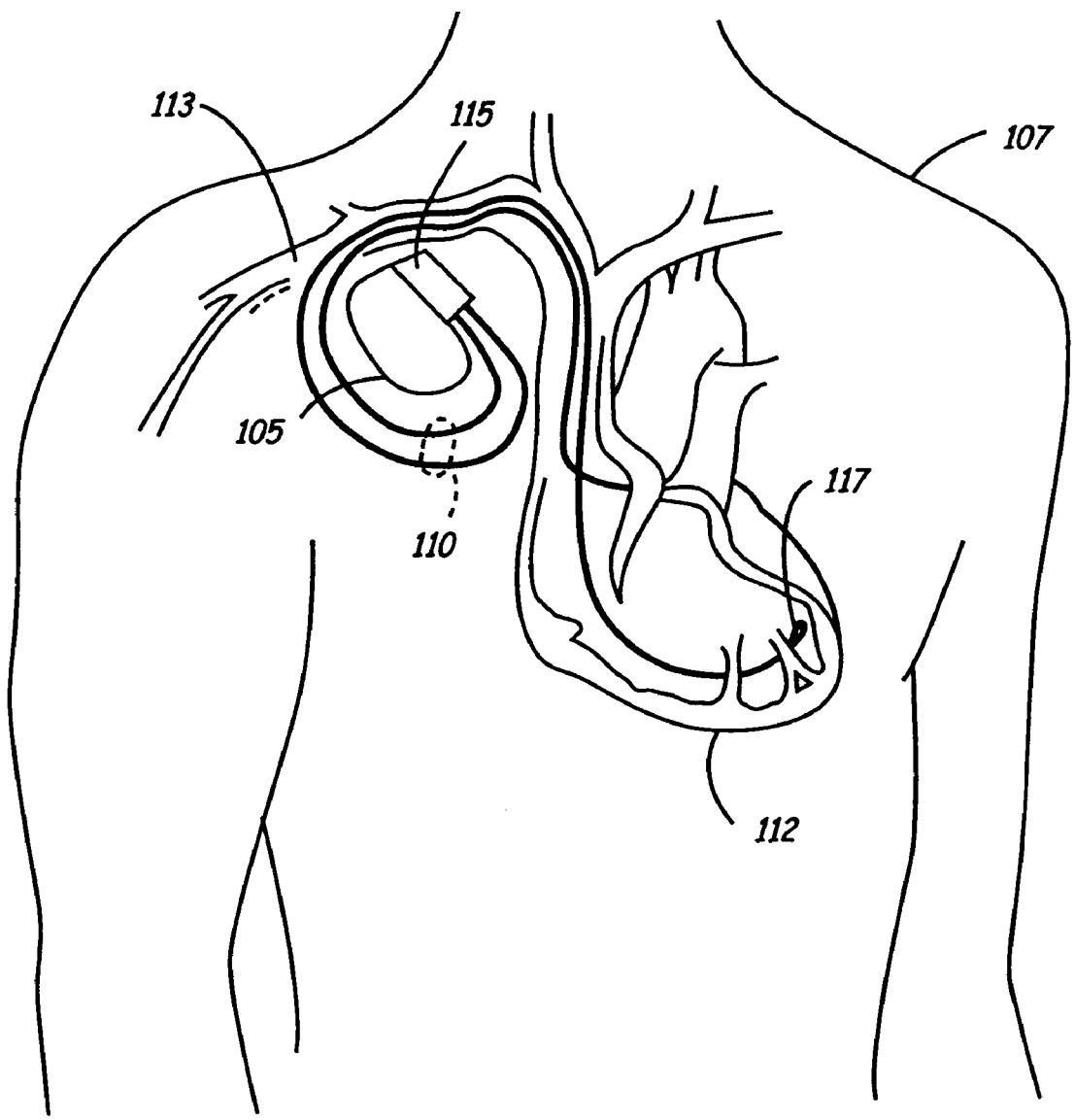
FIG. 1 schematically illustrates an implantable medical device, in the form of a pacemaker, according to one embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but, on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Turning now to the drawings, and specifically referring to FIG. 1, an implantable medical device (IMD) system 100 is shown in accordance with one embodiment of the present invention. The IMD system 100 includes an implantable medical device 105 that has been implanted in a patient 107. In accordance with the illustrated embodiment of the present invention, the implantable device 105 takes the form of a pacemaker for regulating the patient's heart rhythm. Although the implantable device 105 will be discussed in the form of a pacemaker, it will be appreciated that the implantable device 105 may alternatively take the form of a cardioverter, defibrillator, neural stimulator, drug administering device, and the like without departing from the spirit and scope of the present invention.

The implantable device 105 is housed within a hermetically sealed, biologically inert outer housing or container, which may itself be conductive so as to serve as an electrode in the pacemaker's pacing/sensing circuit. One or more pacemaker leads, which are collectively identified by reference numeral 110, are electrically coupled to the implantable device 105 and extend into the patient's heart 112 through a vessel 113, such as a vein. The leads 110 are coupled to the implantable medical device 105 via a connector block assembly 115. Disposed generally near a distal end of the leads 110 are one or more exposed conductive electrodes 117 for sensing cardiac activity and/or delivering electrical pacing stimuli (i.e., therapeutic signals) to the heart 112. The distal end of the lead 110 may be deployed in the ventricle, atrium, coronary sinus, or a cardiac vessel of the heart 112.

Turning now to FIGS. 2A and 2A', a more detailed representation of the distal end of the lead 110 is shown in accordance with one embodiment of the present invention. The lead 110 comprises a flexible electrical conductor 205 for sending diagnostic signals received via the electrode 117 (that may be mounted on the terminal end of the lead 110) to the implantable device 105, and/or for delivering therapeutic signals to the patient via the electrode 117. In one embodiment, the electrical conductor 205 may include tightly coiled stainless steel or a platinum filament. It will be appreciated, however, that the electrical conductor 205 may be constructed from various other suitable materials without departing from the spirit and scope of the present invention.

In accordance with one embodiment of the present invention, the electrical conductor 205 is covered by an electrically insulated sheath or conductor tubing 215 to protect the electrical conductor 205 from bodily fluids of the patient, and to electrically insulate the conductor 205. In one embodiment, the conductor tubing 215 may be constructed from polyurethane. It will be appreciated, however, that the conductor tubing 215 may be constructed from various other materials, such as silicone, for example, without departing from the spirit and scope of the present invention.

In accordance with the illustrated embodiment, a fixation mechanism 220 is provided on the mid or distal portion of the lead 110 to hold the lead 110 substantially stationary within the cardiac vessel of the patient when disposed therein. According to one embodiment, the fixation mechanism 220 comprises a fixation segment 230 that engages and surrounds the conductor tubing 215 of the lead 110. In accordance with the illustrated embodiment, the fixation segment 230 may be constructed of silicone, polyurethane, or the like.

In accordance with one embodiment of the present invention, the fixation segment 230 comprises one or more deployable lobes 240 that are formed lengthwise on the segment 230 by a pair of elongated, parallel cuts or slits 245 made within the fixation segment 230. That is, the deployable lobe 240 is formed between the elongated, substantially parallel slits 245 made within the fixation segment 230 that surrounds the conductor tubing 215. The spacing between the two parallel slits 245 formed within the fixation segment 230 generally defines the width of the deployable lobe 240 formed therebetween. Accordingly, the rigidity of the deployable lobe 240 may be increased by increasing the width of the deployable lobe 240 (i.e., increasing the distance between the parallel slits 245). Additionally, the rigidity of the lobe 240 may be increased by increasing the thickness of the fixation segment 230 that surrounds the conductor tubing 215. Furthermore, the rigidity of the lobe 240 may be altered by using different types of materials for the fixation segment 230. In one embodiment, the end portions of the pair of parallel slits 245 formed within the fixation segment 230 may be joined by a circular cut 250 (within the segment 230) so as to reduce the likelihood of the slits 245 from spreading or expanding along the fixation segment 230. According to one embodiment, slits 245 are cut by a laser.

In accordance with one embodiment of the present invention, push tubing 260 is disposed around the conductor tubing 215 of the lead 110, and is attached to the fixation segment 230 at one end thereof. At the other end of the fixation segment 230, an anchor member 265 is affixed to the conductor tubing 215 to substantially prevent movement of the fixation segment 230 beyond the anchor member 265 (i.e., the anchor member 265 substantially prevents the fixation segment 230 from sliding further down the distal end of the lead 110). In one embodiment, the push tubing 260 may be used to apply compression of the fixation segment 230 against the anchor member 265, by advancing the push tubing 260 toward the distal end of the lead 110. The pushing action on the fixation segment 230 causes the segment 230 to become compressed, thus causing the extension of the deployable lobe 240 outwardly from the outer surface of the fixation segment 230. In an alternative embodiment, the push tubing 260 may be held stationary while the compression of the fixation segment 230 is accomplished by withdrawing the conductor tubing 215 toward the proximal end of the lead 110.

Prior to the lead 110 being placed within a cardiac vessel of the patient, the deployable lobe 240 assumes a retracted position when there is substantially no compression on the fixation segment 230 by the push tubing 260. In the retracted position, the deployable lobe 240 is substantially flat (i.e., not extended outwardly) along the surface of the fixation segment 230. When the lead 110 is placed within the desired site within the cardiac vessel of the patient, the push tubing 260 is pushed toward the distal end of the lead 110. The pushing of the push tubing 260 causes compression of the fixation segment 230 against the anchor member 265, thereby causing the deployable lobe 240 to extend outwardly or protrude from the surface of the fixation segment 230 by assuming an angular flexure or "boomerang" shape (as illustrated in FIG. 2A). In one embodiment, the push tubing 260 may be held in place by using a clip mechanism (not shown) on the proximal end of the lead 110, thereby causing constant compression of the fixation segment 230 by push tubing 260 until the clip mechanism is removed. The deploying of the lobe 240 secures lead 110 within the cardiac vessel and, thus, substantially prevents any movement of the lead 110 within the cardiac vessel.

In an alternative embodiment, lead 110 may have lobe 240 extended outwardly. In other words, in the resting state, lobes 240 would be deployed and during implant the tube is retracted or withdrawn to flatten lobes 240 and relieve all the tension to deploy the lead. When the lead is in a desired position the tubing is pushed to dynamically shape lobes 240 forming an engaging surface thereof. Further, multiple sets of lobes 240 may be located on segments lead 110. In this embodiment, the lengths of segments 245 and the number of slits can vary from subsequent segments of lead 110 on which a series of segments having lobes 240 are located. In yet another embodiment, once the lead is deployed and lobes 240 are in an engaged position, a temporary snap-on clip or an anchoring sleeve may be used for chronic implant. Further, the thickness "t" of lobes 240 could be varied between segments to enable variability in rigidity and resistance at different segments of lead 110 such that each lobe 240 provides varying degrees of flexure.

Figure 2B:
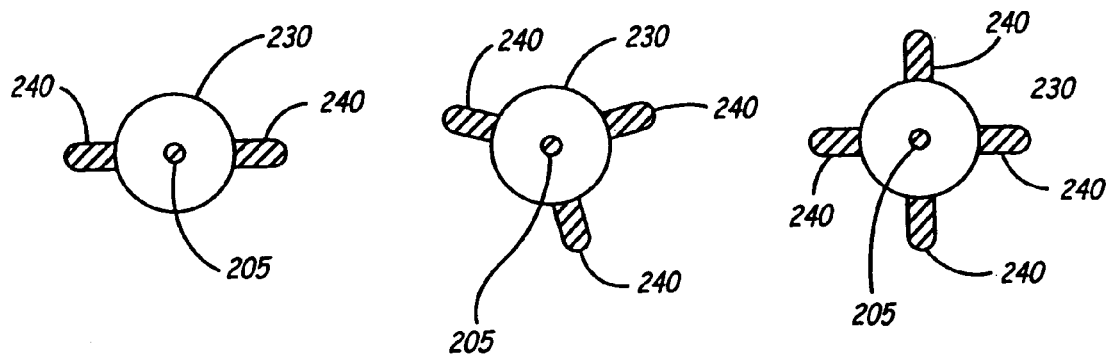
FIGS. 2A, 2A', 2B-D show perspective views of a distal portion of a lead having a deployable lobe for fixating the lead to a vessel according to some embodiments of the present invention.

In accordance with another embodiment of the present invention, more than one deployable lobe 240 may be provided around the circumference of the fixation segment 230 to further secure the lead 110 within the cardiac vessel of the patient (as shown in FIG. 2B). For example, two deployable lobes 240 may be provided on opposite sides of the fixation segment 230, three deployable lobes 240 may be provided at 120-degree separation points around the circumference of the fixation segment 230, or four deployable lobes 240 may be provided at 90-degree separation points around the circumference of the fixation segment 230. It will be appreciated that any number of deployable lobes 240 may be placed around the circumference of the fixation segment 230 to aid in securing the lead 110 within the cardiac vessel. Furthermore, the spacing (i.e., the degree of separation) between the deployable lobes 240 around the circumference of the fixation segment 230 may vary as well. Additionally, the spacing between the deployable lobes 240 around the circumference of the fixation segment 230 need not necessarily be uniform, but may be placed at varying positions around the circumference of the fixation segment 230. It will be further appreciated that the lead 110 may also include two or more fixation segments 230 that are disposed along the distal portion of the lead 110 in series. Accordingly, in this embodiment, each fixation segment 230 will have its own set of deployable lobes 240.

According to the illustrated embodiment, the fixation mechanism 220 may be further configured with a pair of platinum rings 275 (FIG. 2A and 2A'), with each ring 275 disposed around each end of the fixation segment 230 to indicate the degree with which the deployable lobes 240 have been extended outwardly from the surface of the fixation segment 230 under an x-ray examination, for example. Accordingly, if the distance between the platinum rings 275 is minimal, it will indicate that the lobes 240 are deployed (extend outwardly from the surface of the fixation segment 230). In another embodiment, it will be appreciated that the deployable lobes 240 of the fixation segment 230 may be constructed with a radiopaque material, such as barium, platinum or tantalum loaded rubber or polymer, so as to indicate the degree in which the lobes 240 are deployed (in lieu of the platinum rings 275) without departing from the spirit and scope of the present invention.

Figure 2C:
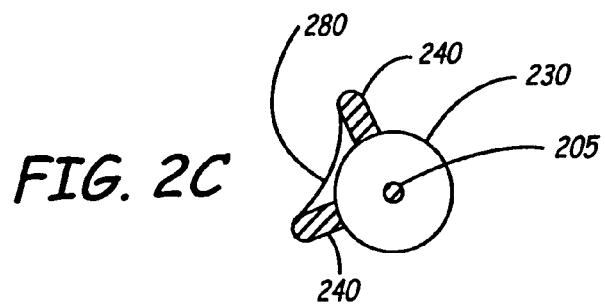
Figure 2D:
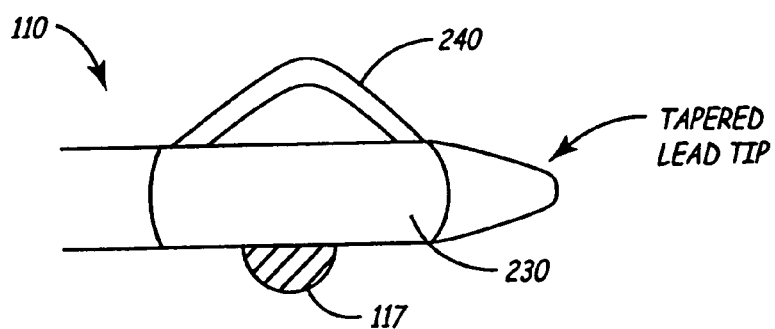

In accordance with one embodiment of the present invention, a webbing material 280 may be attached between two consecutively spaced lobes 240, and deployed when the lobes 240 extend outwardly from the surface of the fixation segment 230 (as shown in FIG. 2C). In another embodiment of the present invention, the electrode 117 may be disposed on the surface of the fixation segment 230 on a side opposite of the deployable lobe 240 (FIG. 2D). In yet another embodiment of the present invention, the terminal end of the lead 110 may be tapered and/or angled to aid in cardiac vessel selection when the electrode 117 is disposed on the surface of the fixation segment 230.

In accordance with another embodiment, a slip coating or clot resistant slip coating may be applied to the inner surface of the push tubing 260 or to the outer surface of the conductor tubing 215 to facilitate the sliding of the push tubing 260 over the conductor tubing 215. According to one embodiment, the slip coating may take the form of polyacrylamide, PVP, or heparin polyacrylamide hydrophilic coating, or polytetrafluroethylene (PTFE); however, it will be appreciated that the slip coating or slip and anti-coagulant combination coating may include various other equivalent materials without departing from the scope of the present invention.

Turning now to FIG. 3A, a fixation mechanism 300 for the lead 110 is shown in accordance with another embodiment of the present invention. In this particular embodiment, the distal end of the lead 110 is configured with at least one deployable lobe 305 that may extend outwardly so as to protrude from the surface of the conductor tubing 215. In one embodiment, the portion of the conductor tubing 215 that covers the deployable lobe 305 comprises a flexible material 310. In accordance with one embodiment, the flexible material 310 is provided in the form of a balloon-like material (such as polyisoprene, polyurethane, or silicone, for example) that may stretch when the deployable lobe 305 is extended outwardly from the surface of the conductor tubing 215. In one embodiment, the deployable lobe 305 may be fixedly attached to the electrical conductor 205 at a point 306, and provided with a joint 308 to permit the deployable lobe 305 to be substantially parallel with the conductor tubing 215 when assuming a retracted position or to extend outwardly or protrude from the surface of the conductor tubing 215 by assuming an angular or "boomerang" shape (as depicted in FIG. 3A). Alternatively, the deployable lobe 305 at the point 306 may be fixedly attached to a "stopper" mechanism (not shown) disposed within the conductor tubing 215, as opposed to be attached to the electrical conductor 205 (as shown in FIG. 3A), without departing from the spirit and scope of the present invention. It will further be appreciated, in another embodiment, that the flexible material 310 may be omitted from covering the deployable lobe 305 providing that the electrical conductor 205 is covered with an insulating material to protect the conductor 205 from bodily fluids of the patient.

In accordance with the illustrated embodiment, the conductor tubing 215 comprises a bilumen tubing, with a first lumen 317 accommodating the electrical conductor 205 and a second lumen 318 for accommodating a push-pull wire 320 for actuating the deployable lobe 305. Prior to the lead 110 being placed within a cardiac vessel of the patient, the deployable lobe 305 is retracted by pulling the push-pull wire 320 within the lumen 318. In the retracted position, the deployable lobe 305 assumes a substantially linear (or straightened) position, where the flexible material 310 is not extended outwardly from the conductor tubing 215 of the lead 110. When the lead 110 is placed at the desired site within the cardiac vessel, the push-pull wire 320 is pushed within the lumen 318 toward the deployable lobe 305. The pushing of the push-pull wire 320 within the lumen 318 causes the deployable lobe 305 to extend outwardly or protrude from the surface of the conductor tubing 215 by assuming an angular or "boomerang" shape. As the deployable lobe 305 extends outwardly or protrudes from the surface of the conductor tubing 215, the deployable lobe 305 stretches the flexible material 310 resting thereon. The push-pull wire 320 is pushed within the lumen 318 until the apex of the deployable lobe 305 engages the cardiac vessel, thereby securing the lead 110 within the cardiac vessel and, thus, substantially preventing any movement of the lead 110 therein.

It will be appreciated that more than one deployable lobe 305 may be provided for the lead 110 to further secure the lead 110 within the cardiac vessel (as shown in FIG. 3B). For example, two deployable lobes 305 may be provided on opposite sides of the lead 110, three deployable lobes 305 may be provided at 120-degree separation points around the circumference of the lead 110, or four deployable lobes 305 may be provided at 90-degree separation points around the circumference of the lead 110. It will further be appreciated that any number of deployable lobes 305 may be placed around the circumference of the lead 110 to aid in securing the lead 110 within the cardiac vessel. Furthermore, the spacing (i.e., the degree of separation) between the deployable lobes 305 around the circumference of the lead 110 may vary as well. Additionally, the rigidity of the deployable lobe 305 may be altered by increasing or decreasing the width of the deployable lobe 305.

In accordance with one embodiment of the present invention, the electrode 117 may be placed on the terminal end of the lead 110. In another embodiment, the electrode 117 may be placed on a side of the lead 110 opposite from the side the deployable lobe 305 (in the case where one deployable lobe 305 is utilized) for the fixation mechanism 300 (as shown in FIG. 3C).

Figure 4A:
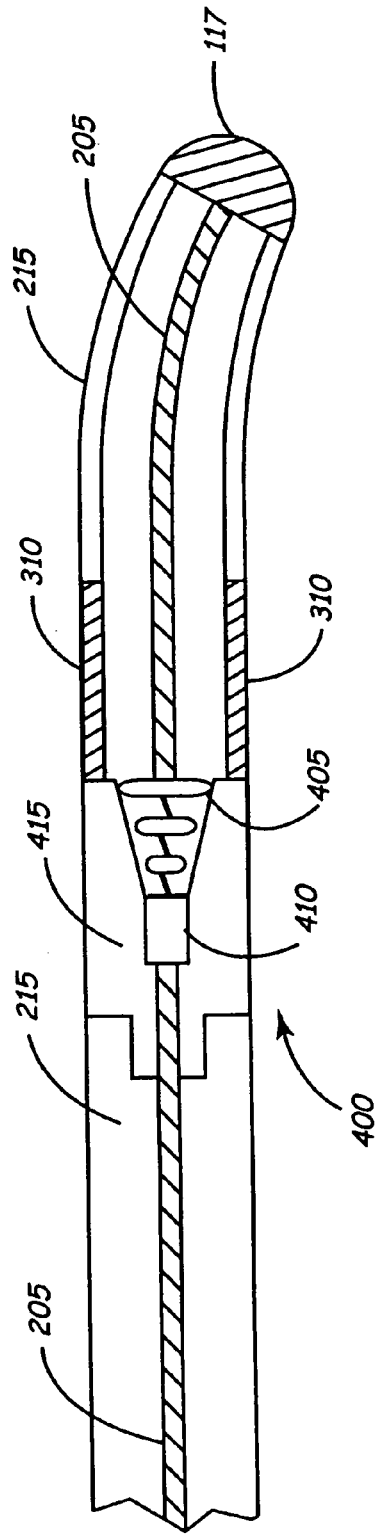
FIGS. 4A-B show a side view perspective of the distal portion of the lead employing an expandable spring for fixating the lead to the vessel in accordance with another embodiment of the present invention.

Turning now to FIG. 4A, a fixation mechanism 400 for the lead 110 is shown in accordance with another embodiment of the present invention. In this particular embodiment, the distal end of the lead 110 is configured with an expandable spring 405 that encircles the electrical conductor 205 and is attached thereto by a crimp bus 410. In accordance with the illustrated embodiment, the expandable spring 405 is housed within a sleeve head 415 when the expandable spring 405 assumes a retracted position. A portion of the conductor tubing 215 includes the flexible material 310, such as a stretchable balloon-like material, for example, which is capable of expanding beyond the diameter of the conductor tubing 215 when the expandable spring 405 is pushed out from the sleeve head 415.

Figure 4B:
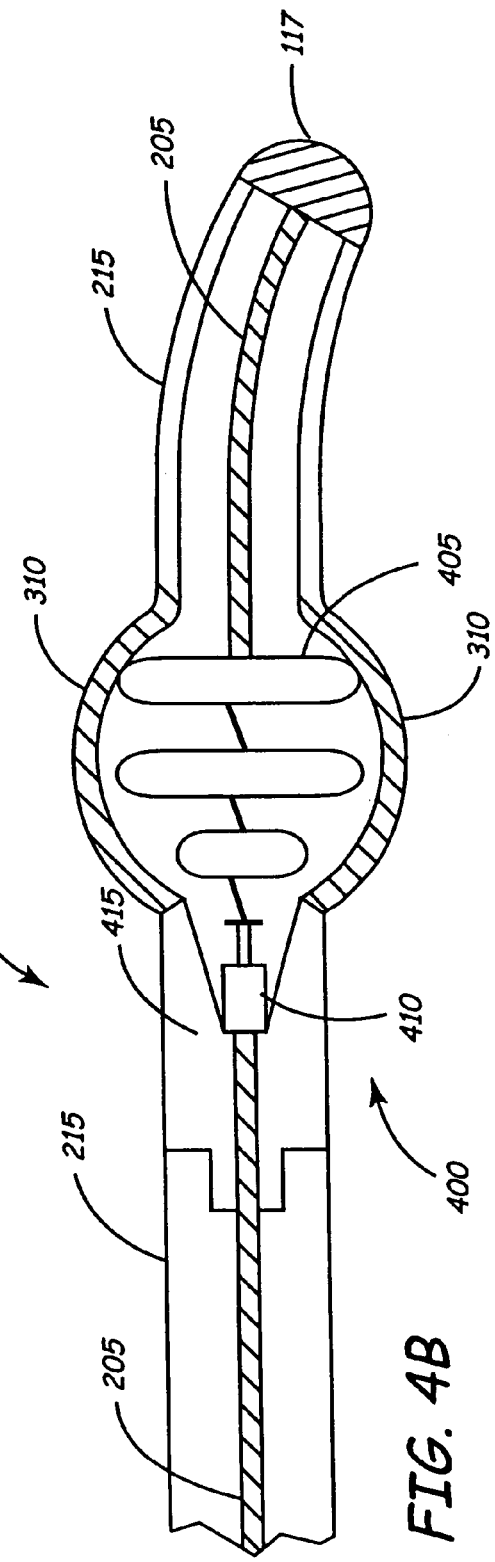

Prior to the lead 110 being placed within a cardiac vessel of the patient, the expandable spring 405 is retracted within the sleeve head 415 by rotating the electrical conductor 205 in one direction (e.g., counter-clockwise). In the retracted position, the expandable spring 405 is compressed by the sleeve head 415, and the flexible material 310 attached to the conductor tubing 215 is not extended outwardly from the conductor tubing 215 of the lead 110 (i.e., the flexible material 310 has substantially the same diameter as the conductor tubing 215). When the lead 110 is placed at the desired site within the cardiac vessel, the electrical conductor 205 is rotated in the other direction (e.g., clockwise), which causes the expandable spring 405 to be ejected from the sleeve head 415, and causes the spring 405 to expand the flexible material 310 outwardly or protrude from the surface of the conductor tubing 215 (as shown in FIG. 4B). As the expandable spring 405 extends outwardly from the surface of the conductor tubing 215, the spring 405 stretches the flexible material 310 resting thereon. The electrical conductor 205 is rotated until the flexible material 310 engages the cardiac vessel, thereby securing the lead 110 within the cardiac vessel 113 and, thus, substantially preventing any movement of the lead 110 therein. In another embodiment of the present invention, it will be appreciated that the flexible material 310 may be placed underneath the expandable spring 405 and the exposed spring 405 may be further used as an electrode.

Turning now to FIG. 5A, a fixation mechanism 500 is shown in accordance with another embodiment of the present invention. In this particular embodiment, the distal end of the lead 110 is configured with a stent 505 that may be expanded so as to protrude from the surface of the conductor tubing 215 (as shown in FIG. 5B). In one embodiment, the portion of the conductor tubing 215 that covers the stent 505 comprises a flexible material 310. In accordance with the illustrated embodiment, the flexible material 310 is provided in the form of a balloon-like material that may stretch when the stent 505 is expanded outwardly from the surface of the conductor tubing 215. In one embodiment of the present invention, the stent 505 may take the form of a spring or coil. In another embodiment, the stent 505 may be placed around the conductor tubing 215 as opposed to being located within the conductor tubing 215.

Prior to the lead 110 being placed within a cardiac vessel of the patient, the stent 505 assumes an unexpanded state by rotating the electrical conductor 205 in one direction (e.g., in a counter-clockwise direction). In the unexpanded state, the diameter of the stent 505 substantially matches the diameter of the conductor tubing 215 of the lead 110, where the flexible material 310 is not stretched or expanded outwardly therefrom. When the lead 110 is placed within the cardiac vessel at the desired site, the electrical conductor 205 is rotated in the opposite direction (e.g., a clockwise direction), which causes the stent 505 to expand in diameter. When the diameter of the stent 505 is expanded so as to exceed the diameter of the conductor tubing 205, the flexible material 310 resting thereon expands outwardly from the surface of the conductor tubing 215. As the stent 505 expands or protrudes from the surface of the conductor tubing 215, the stent 505 stretches the flexible material 310 resting thereon. The electrical conductor 205 is rotated until the stent 505 and the flexible material 310 resting thereon engages the cardiac vessel, thereby securing the lead 110 within the cardiac vessel and substantially preventing any movement of the lead 110 therein.

Turning now to FIG. 6A, a fixation mechanism 600 is shown in accordance with another embodiment of the present invention. In this particular embodiment, the distal end of the lead 110 is configured with a deployable lobe 605 that may be expanded so as to protrude from the outer surface of the conductor tubing 215. In one embodiment, the deployable lobe 605 takes the form of a balloon that resides on a side surface of the conductor tubing 215 of the lead 110. In an alternative embodiment, the deployable lobe 605 may be configured so as to surround the circumference of the lead 110. In the illustrated embodiment, the conductor tubing 215 comprises a bilumen tubing with a first lumen 612 accommodating the electrical conductor 205 and a second lumen 613 with a port 620 used for injecting a gas or liquid solution within the second lumen 613 to expand the deployable lobe 605.

In accordance with one embodiment of the present invention, prior to the lead 110 being placed within a cardiac vessel of the patient, the deployable lobe 605 remains deflated on the side-surface of the conductor tubing 215 of the lead 110 (as shown in FIG. 6A). When the lead 110 is placed at a desired site within the cardiac vessel, a liquid solution or gas is injected into the lumen 613 via the port 620. In accordance with one embodiment, the liquid solution may include saline and the gas may include carbon dioxide. It will be appreciated, however, that various other liquid solutions or gases may be used in lieu of the examples provided without departing from the spirit and scope of the present invention.

The injecting of the solution or gas within the lumen 613 causes the deployable lobe 605 to expand by filling the lobe 605 with the solution or gas and, thus, protrude or expand outwardly from the outer surface of the conductor tubing 215 (as shown in FIG. 6B). The solution or gas is injected through the port 620 until the deployable lobe 605 engages the cardiac vessel, thereby securing the lead 110 within the cardiac vessel and, thus, substantially preventing any movement of the lead 110 therein. Subsequent to filling the deployable lobe 605 with the desired amount of solution or gas, the port 620 may be removed, and the lumen 613 may be sealed at the opening formed by the port 620 with an adhesive or a self-sealing rubber grommet, for example, so as to prevent any leakage of the solution or gas from the lumen 613 (and, thus, preventing the deployable lobe 605 from deflating). In accordance with another embodiment, the conductor tubing 215 may be provided as a single lumen, and the deployable lobe 605 may be provided with an opening (not shown) therein to inject a gas or solution to inflate the deployable lobe 605. In this particular embodiment, the opening within the deployable lobe 605 may then be sealed to prevent any leakage of the gas or solution injected therein, and, thus, substantially prevent deflation of the deployable lobe 605.

In accordance with one embodiment, the electrode 117 may be placed on the terminal end of the lead 110. In another embodiment, the electrode 117 may be placed on a side of the lead 110 opposite from the side the deployable lobe 605 on the lead 110.

Turning now to FIG. 7A, a fixation mechanism 700 for the lead 110 is shown in accordance with another embodiment of the present invention. In this particular embodiment, the distal end of the lead 110 is configured with a pair of deployable lobes 705 that may extend outwardly so as to protrude from the surface of the conductor tubing 215. Although two deployable lobes 705 are shown in FIG. 7A, it will be appreciated that only one or more than two deployable lobes 705 may be disposed around the circumference of the conductor tubing 215 without departing from the spirit and scope of the present invention.

In one embodiment, the deployable lobe 705 may take the form of a flange, and may be fixedly attached to a fixation segment 708 that is engaged with and encircles the conductor tubing 215. In one embodiment, the deployable lobe 705 may be constructed out of a plastic (e.g., silicone or some other polymer) or may be constructed out of a metal. The deployable lobe 705 may be fixedly attached to the fixation segment 708 at a pivot point 706 to allow the deployable lobe 705 to be substantially parallel to the surface of the conductor tubing 215 when assuming a retracted position or to extend outwardly or protrude from the surface of the conductor tubing 215 when the deployable lobe 705 is extended outwardly from the surface of the conductor tubing 215 (i.e., when the deployable lobe 705 rotates about the pivot point 706). Push tubing 710 surrounds the conductor tubing 215, and an end portion 715 of the push tubing 710 engages an inner edge 717 of the deployable lobe 705.

In the illustrated embodiment, the inner edge 717 of the deployable lobe 705 is sloped or tapered so as to cause the deployable lobe 705 to eject outwardly when the end portion 715 of the push tubing 710 slides between the outer surface of the conductor tubing 215 and the inner edge 717 of the deployable lobe 705. That is, when the push tubing 710 is pushed towards the distal end of the lead 110, the end portion 715 of the push tubing 710 slides between the outer surface of the conductor tubing 215 and the inner edge 717 of the deployable lobe 705, thereby causing the lobe 705 to rotate about the pivot point 706 and extend outwardly from the outer surface of the conductor tubing 215.

When the push tubing 710 is pulled away from the distal end of the lead 110, the deployable lobe 705 will retract until the deployable lobe 705 is substantially parallel to the outer surface of the conductor tubing 215. A slip coating may be applied to the inner surface of the push tubing 710 or to the outer surface of the conductor tubing 215 to facilitate the sliding of the push tubing 710 over the conductor tubing 215. According to one embodiment, the slip coating may take the form of polyacrylamide or polytetrafluroethylene (PTFE); however, it will be appreciated that the slip coating may include various other materials. In the illustrated embodiment, a molded transitional piece 720 is provided between the deployable lobe 705 and the outer surface of the conductor tubing 215 to provide a gradual transition between the outer surface of the conductor tubing 215 and the deployable lobe 705.

In one embodiment, the end portion 715 of the push tubing 710 is tapered so as to facilitate the passage of the end portion 715 of the push tubing 710 underneath the deployable lobe 705. Furthermore, the distal tip of the deployable lobe 705, which engages the cardiac vessel when the lobe 705 is extended outwardly, may be rounded to prevent damage to the cardiac vessel when engaged therewith.

In one embodiment of the present invention, the deployable lobe 705 may be covered by flexible material 310 that is attached to the molded transition piece 720 and the push tubing 710 to reduce the likelihood of tissue in growth or bodily fluids of the patient from ingressing underneath the push tubing 215. In accordance with one embodiment, the flexible material 310 is provided in the form of a balloon-like material (such as polyisoprene, polyurethane, or silicone, for example) that may stretch when the deployable lobe 705 is extended outwardly from the surface of the conductor tubing 215. In accordance with an alternative embodiment, it will be appreciated that the flexible material 310 may be omitted, if so desired.

Prior to the lead 110 being placed within a cardiac vessel of the patient, the deployable lobes 705 are retracted by pulling the push tubing 710 away from the distal end of the lead 110. In the retracted position, the deployable lobe 705 assumes a substantially parallel position relative to the outer surface of the conductor tubing 215, where the deployable lobe 705 is not extended outwardly from the conductor tubing 215 of the lead 110. When the lead 110 is placed at the desired site within the cardiac vessel, the push tubing 710 is pushed toward the distal end of the lead 110. This pushing action will cause the end portion 715 of the push tubing 710 to slide under the deployable lobe 705, which will cause the deployable lobe 705 to extend outwardly or protrude from the surface of the conductor tubing 215 rotating outwardly about the pivot point 706. As the deployable lobe 705 extends outwardly or protrudes from the surface of the conductor tubing 215, the deployable lobe 705 stretches the flexible material 310 resting thereon. The pushing action of the push tubing 710 resumes until the distal tip of the deployable lobe 705 engages the cardiac vessel, thereby securing the lead 110 within the cardiac vessel. It will be appreciated that the push tubing 710 may be held in place with a clip mechanism (not shown), as discussed previously.

Turning now to FIG. 7B, the fixation mechanism 700 is shown in accordance with another embodiment of the present invention. In this particular embodiment, a unipolar lead 740 is surrounded by an outer coil 745, and an outer tubing 750 surrounds the outer coil 745. By rotating the outer coil 745 in one direction (i.e., clockwise, for example), it will cause the end portion 752 of the outer tubing 750 to go under the deployable lobe 705 and cause the lobe 705 to extend outwardly from the outer tubing 750 when the lobe 705 rotates about the pivot point 706 as illustrated in FIG. 7C. When it is desired to retract the lobe 705 such that it becomes substantially parallel with the surface of the outer tubing 750, the outer coil 745 may be rotated in the opposite direction (i.e., counter-clockwise, for example) to cause the outer tubing 750 to disengage from underneath the deployable lobe 705, and thus cause the lobe 705 to retract and become substantially parallel in relation to the surface of the outer tubing 750.

Figure 8A:
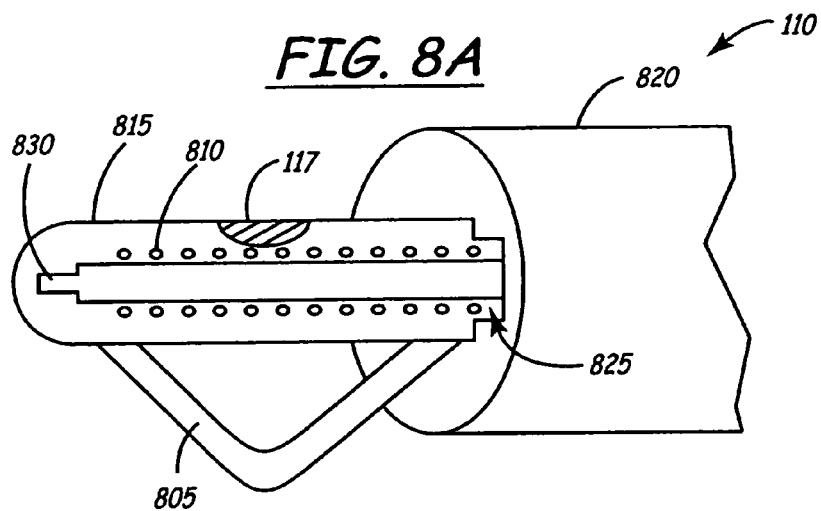
FIGS. 8A-D show perspective views of a distal portion of a lead having a deployable lobe for fixating the lead to a vessel according to another embodiment of the present invention.

Turning now to FIG. 8A, a fixation mechanism 800 for the lead 110 is shown in accordance with another embodiment of the present invention. In this particular embodiment, the distal end of the lead 110 is configured with at least one deployable lobe 805 that may extend outwardly so as to protrude from the surface of a conductor tubing 815 that surrounds an electrical conductor 810. In one embodiment, the deployable lobe 805 takes the form of a polyurethane strip material that may be fixedly attached to the outer surface of the conductor tubing 815 at each end of the lobe 805. It will be appreciated that the deployable lobe 805, as opposed to being provided in the form of a polyurethane strip, may be constructed out of various other materials, such as silicone, for example, without departing from the spirit and scope of the present invention.

Figure 8B:
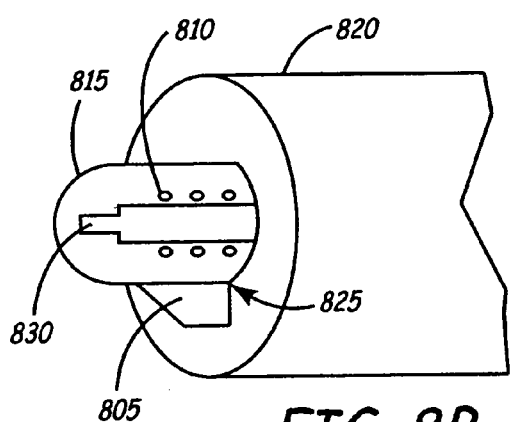
Figure 8D:
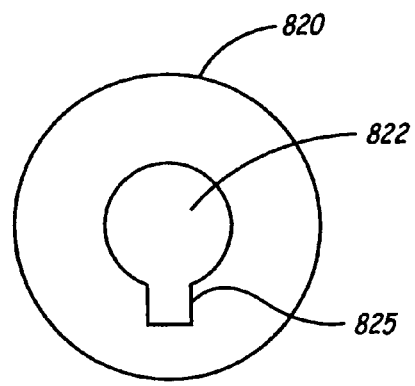

In accordance with the illustrated embodiment, the electrical conductor 810 is slideably received within an opening of an outer tubing 820 that surrounds the electrical conductor 810. Referring to FIG. 8B, the deployable lobe 805 is shown in the retracted position, where the lobe 805 is received within a recessed slot 825 formed within the opening of the outer tubing 820. FIG. 8D illustrates a cross-sectional view of the outer tubing 820 with the opening 822 in which the electrical conductor 810 is slideably received and the recessed slot 825 formed within the opening 822 for receiving the deployable lobe 805.

Figure 8C:
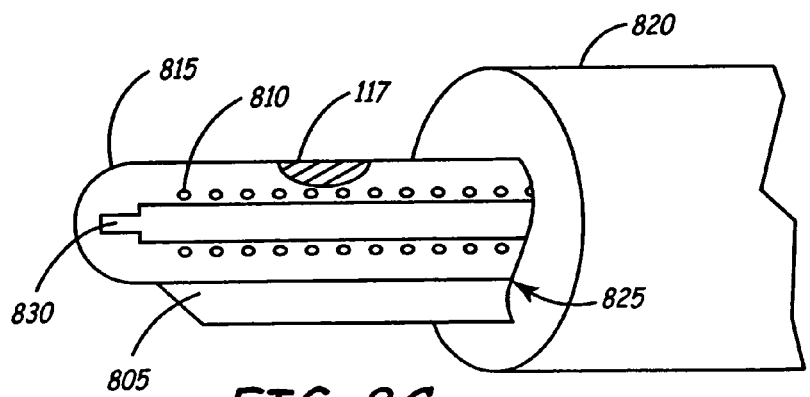

Typically, the electrical conductor 810 will have a natural tendency to remain retracted within the opening 822 of the outer tubing 820. A stylet (not shown) is utilized to push out the electrical conductor 810 from the opening 822 of the outer tubing 820, as is conventional in the art. FIG. 8C shows the electrical conductor 810 extended from the opening 822 of the outer tubing 820. When the electrical conductor 810 is extended from the opening 822 of the outer tubing 820 using the stylet, the deployable lobe 805 on the outer surface of the conductor tubing 815 is exposed. Once the deployable lobe 805 is exposed, the electrical conductor 810 may then be rotated either clockwise or counter-clockwise using the stylet (not shown) within a recessed opening 830 of the electrical conductor 810. By rotating the electrical conductor 810, the deployable lobe 805 is no longer in alignment with the recessed slot 825, and, therefore, may not be received within the slot. Subsequent to rotation by the stylet, the electrical conductor 810 will attempt to retract within the opening 822 of the outer tubing 820, and because the deployable lobe 805 is not in alignment with the recessed slot 825, will cause the deployable lobe 805 to extend outwardly (or "buckle") from the outer surface of the conductor tubing 815 (as illustrated in FIG. 8A).

Prior to the lead 110 being placed within a cardiac vessel of the patient, the deployable lobe 805 assumes a retracted position within the recessed slot 825 of the outer tubing 820 as illustrated in FIG. 8B. In the retracted position, the deployable lobe 805 assumes a substantially parallel position relative to the outer surface of the conductor tubing 815, where the deployable lobe 805 is not extended outwardly from the surface of the conductor tubing 815 of the lead 110. When the lead 110 is placed at the desired site within the cardiac vessel, a stylet (not shown) is used to push out the electrical conductor 810 from the opening 822 of the outer tubing 820 until the deployable lobe 805 is exposed (as illustrated in FIG. 8C). The stylet is then used to rotate the electrical conductor 810 either clockwise or counter-clockwise until the deployable lobe 805 is no longer in alignment with the recessed slot 825 formed within the opening 822 of the outer tubing 820. When the stylet is removed, the electrical conductor 810 will naturally attempt to retract within the opening 822 of the outer tubing 820. Because the deployable lobe 805 is not in alignment with the recessed slot 825 of the opening 822 of the outer tubing 820, the deployable lobe 805 will extend outwardly from the outer surface of the conductor tubing 815 (as illustrated in FIG. 8A), thereby causing the apex of the lobe 805 to engage the side of the cardiac vessel and fixedly secure the lead 110 therein.

FIG. 9A is a plan view of a lead 900 including a fixation mechanism 920, similar to mechanism 220 described in conjunction with FIGS. 2A and 2A', according one embodiment of the present invention. FIG. 9A illustrates lead 900 including a lead body 950 having a proximal portion 91, to which a connector 905 is coupled, a distal portion 92, to which an electrode 925 is coupled, and a fixation mechanism 920 extending from proximal portion 91 to distal portion 92. According to one embodiment, lead body 950 is formed by an outer insulative sheath 915 surrounding a coil conductor 955 (FIG. 12) extending from electrode 925 to connector 905 and coupling electrode 925 to a contact of connector 905. FIG. 9A further illustrates fixation mechanism 920 including a proximal end 910, a distal end 915, three fixation segments 230, positioned in proximity to distal end 915, anchor member 265 and a push tube segment 960 extending from fixation segments 230 proximally to proximal end 910 where segment 960 is terminated in a retention sleeve 961. According to embodiments of the present invention, retention sleeve 961 includes features adapted to create a frictional interface between fixation mechanism 920 and lead body 950 as will be described in conjunction with FIG. 10. Retention sleeve 961 may be formed as an independent component, separate from push tube 960 and subsequently fixedly coupled to push tube 960, or may be formed as an integral segment of push tube 960. It should be noted that each feature of sleeve 961, described below, may be incorporated directly into push tube 960, alone or in combination, according to various embodiments of the present invention.

FIG. 9B is a perspective view of a distal portion of the lead shown in FIG. 9A wherein fixation mechanism 920 is deployed, according to one embodiment, by advancing push tube 960 distally, per arrow A, to compress deployable lobes 240 of each fixation segment 230 between push tube 960 and anchor member 265, which, for example may be an adhesive bond between distal end 915 of fixation mechanism 920 and lead body 950. Embodiments of fixation segments 230 and deployable lobes 240 are described in conjunction with FIGS. 2A and 2A'. According to one embodiment, a sidewall of at least push tube 960 portion of fixation mechanism 920 includes a filler material making the sidewall opaque such that fixation mechanism 920 can be easily visually distinguished from lead body 950.

Figure 10A:
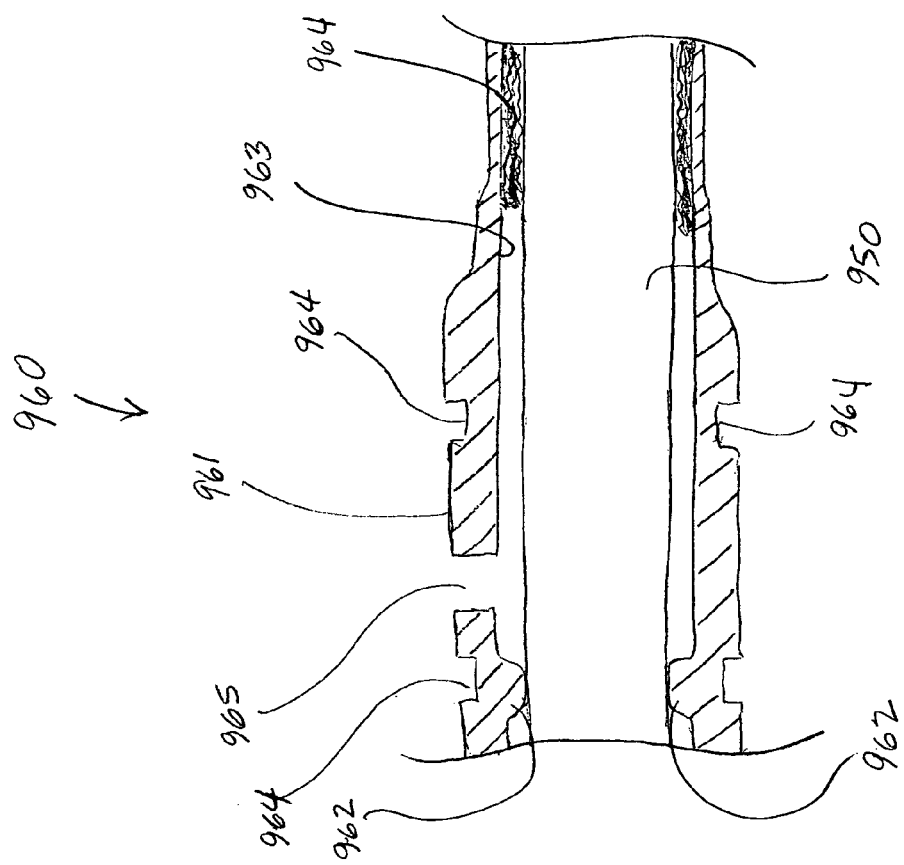
FIG. 10A is a partial section view through section line A-A shown in FIG. 9A.

FIG. 10A is a partial section view through section line A-A shown in FIG. 9A. FIG. 10A illustrates the frictional interface formed between retention sleeve 961 and lead body 950 by means of an internal protrusion 962 engaging a surface of lead body 950. Protrusion 962 may extend all the way around a circumference of lead body 950 or only partially around the circumference; furthermore multiple protrusions 962 of either type may be arranged within an inner surface 963 of sleeve 961. According to one embodiment, protrusion 962 only serves to prevent push tube 960 from sliding distally when lead 900 is in a package or being handled prior to fixation mechanism deployment during implant; according to another embodiment, protrusion 962, extending all the way around the circumference of lead body 950, further forms a fluid tight seal preventing bodily fluids which may enter a space between push tube 960 and lead body 950, through lobes 240, to flow proximally from out from the space; in either case, the frictional interface does not engage lead body 950 so as to prevent purposeful activation of push tube 960. According to an alternate embodiment illustrated in FIG. 10B, inner surface 963 of sleeve 961 forms an oval or ellipse wherein a frictional interface 93, between sleeve 961 and lead body 950, is formed along a minor axis 94 of the oval or ellipse and is released for activation of push tube 960 upon compression along a major axis 95, per arrows C, which spreads inner surface 963 of sleeve 961 away from lead body along minor axis 94, per arrows D.

FIG. 10A further illustrates sleeve 961 including a port 965, which may be formed by laser ablation or mechanical drilling, passing through a sidewall of sleeve 961 and thus providing access to the space between push tube 960 and lead body 950. According to one embodiment of the present invention, port 965 is adapted to receive an infusion of fluid intended for passage distally between push tube 960 and lead body 950; the fluid may be a therapeutic agent or a diagnostic agent, i.e. contrast agent, dispersed out from fixation mechanism 920 in proximity to distal end 915 during an implant procedure, or the fluid may one adapted to reduce friction between tube 960 and body 950 to facilitate deployment of fixation mechanism 920 during the procedure, for example a lubricant. In conjunction with port 965, protrusion 962 may form fluid tight seal about lead body 950 to prevent backflow of infused fluid out from proximal end 910 of fixation mechanism 920. According to another embodiment, port 965 is adapted to vent the space between lead body 950 and push tube 960 facilitating activation of fixation mechanism 920 when protrusion 962 forms a fluid tight seal about lead body 950; according to the embodiment illustrated in FIGS. 9A-B, port 965 acting as a vent may further allow flow of bodily fluid, entering in proximity to distal end 915, to create a lubricious interface 964 between push tube 960 and lead body 950, the lubricious interface further facilitating activation of fixation mechanism 920. According to alternate embodiments of the present invention push tube 960 includes a plurality of ports and may be formed of porous material.

According to some embodiments of the present invention, lubricious interface 964 is formed by a hydrophilic coating present on an inner surface of fixation mechanism 920 or on outer surface of lead body 950. According to one exemplary embodiment an outer diameter of lead body 950 is approximately 0.044 inch, a major inner diameter of fixation mechanism 920 is approximately 0.056 inch, a minor inner diameter, that is, at protrusion 962, is approximately 0.042 inch, an overall length of inactivated fixation mechanism 920 ranges from approximately 26 inches to approximately 36 inches (dependent upon an overall length of lead 900) and a diameter of port 965 is approximately 0.03 inch to vent the space between push tube 960 and lead body 950. Furthermore, fixation mechanism 920, according to this embodiment, is formed from polyurethane having a hardness of 55D and outer insulation 915 (FIG. 12) of lead body 950 is formed from polyurethane having a hardness of 55D. This exemplary embodiment further includes a polyacrylamide coating covalently bound, grafted by a ceric ion initiation process, to an inner surface of fixation mechanism 920 (prior to assembling fixation mechanism 920 onto lead body 950); in one case, the ceric ion is from ceric ammonium nitrate which initiates polymerization of an acrylamide monomer onto the inner surface, and the grafting is carried out by a pump and manifold flow-through process followed by a water rinse to remove any unpolymerized acrylamide. Venting via port 965 allows bodily fluid, entering into gaps between lobes 240 of fixation elements 230, to flow into the space between push tube 960 and lead body 950 and thus hydrate the hydrophilic polyacrylamide coating during the implant procedure; however, we have found that this coating need not be hydrated to reduce friction between push tube 960 and lead body 950. Alternatively, a saline solution may be injected between tube 960 and body 950 via port, to hydrate the polyacrylamide coating. According to an alternate embodiment, a fluoropolymer liner, which is either incorporated within fixation mechanism 920 or overlaying lead body 950, forms lubricious interface 964 and a fluid is not required to hydrate or lubricate the interface.

FIG. 10A further illustrates sleeve 961 including retention grooves 964 formed on an outer surface thereof; grooves 964 are adapted to receive a retaining element, which engage grooves to press sleeve 961 against lead body 950, thereby fixedly retaining fixation mechanism 920 in a prescribed position upon lead body 950, for example in the position illustrated in FIG. 9B wherein lobes 240 are deployed for fixation of lead 900 at an implant site. According to one embodiment of the present invention, the retaining element includes a suture tied about each groove 964; according to another embodiment the retaining element includes a spring clip fitted about each groove 964. According to yet another embodiment, one of grooves 964 accommodates a holding tool, for example tool 97 illustrated in FIG. 11.

Figure 11:
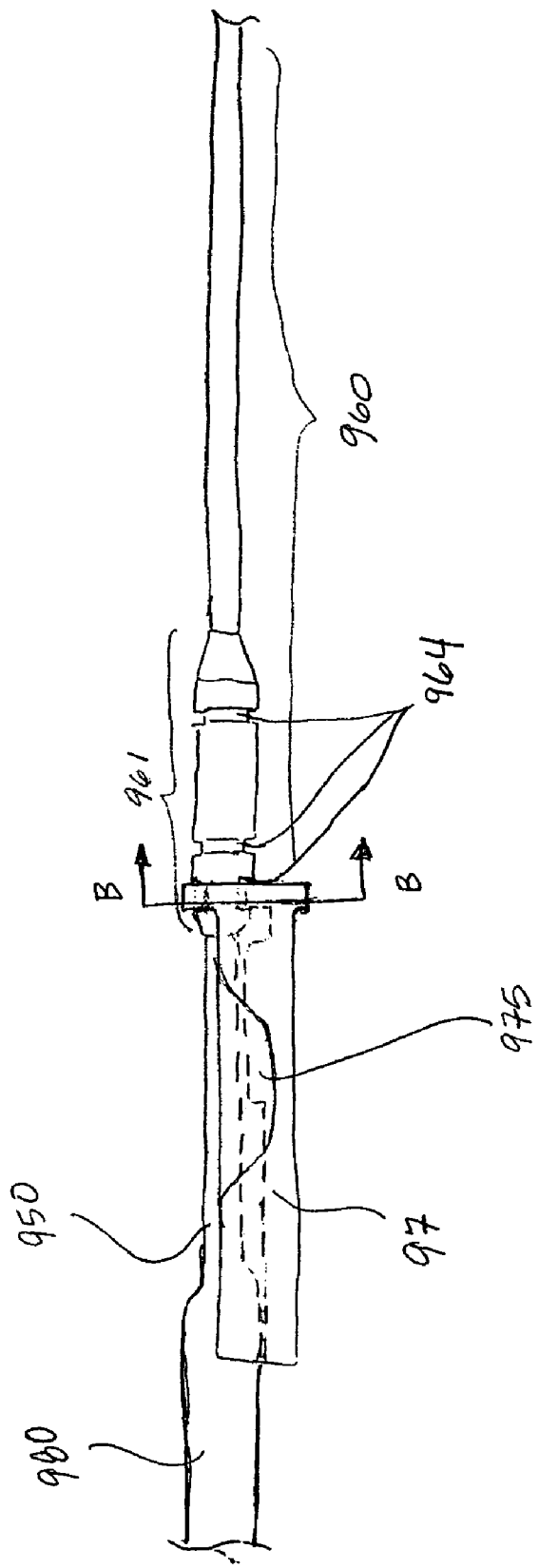
FIG. 11 is a partial plan view of the lead shown in FIG. 9A further including a holding tool according to one embodiment of the present invention.
Figure 12:
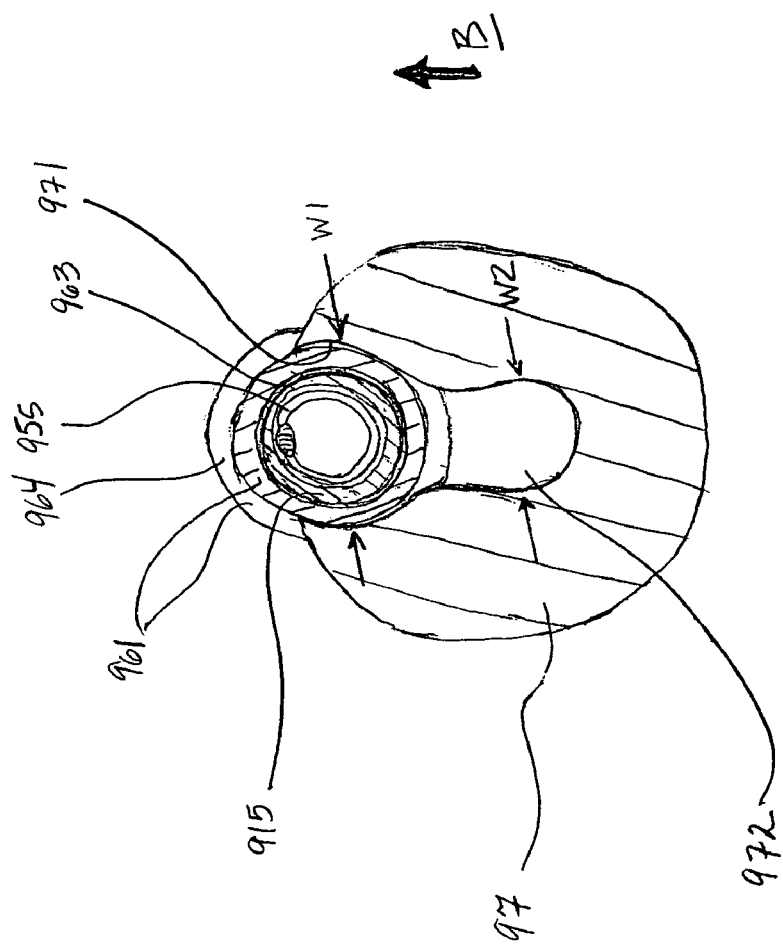
FIG. 12 is a section view through section line B-B shown in FIG. 11.

FIG. 11 is a partial plan view of the lead shown in FIG. 9A, further including a holding tool 97 according to one embodiment of the present invention; and FIG. 12 is a section view through section line B-B shown in FIG. 11. FIG. 11 illustrates holding tool 97 fitted onto sleeve 961 and including a gripping surface 975 (formed by a necked-in region) accommodating operator handling of fixation mechanism 920. According to the illustrated embodiment, holding tool 97 includes a first end engaged in retention groove 964 of sleeve 961 and a second end loosely fitted around lead body 950 and a connector sleeve 980, which couples connector 905 (FIG. 9A) to lead body 950; in a first position, as illustrated in the section view of FIG. 12, tool 97 holds sleeve 961 within a slot first portion 971 formed in the first end of tool 97. Slot first portion 971 includes a width W1 necessary to hold onto sleeve 961 during push tube activation of fixation mechanism 920 and may further create a frictional interface between inner surface 963 and lead body 950 (lead body 950 shown in FIG. 12 as a combination of conductor 955 surrounded by outer insulative sheath 915) so as to prevent push tube 960 from sliding distally when lead 900 is in a package or being implanted, prior to fixation mechanism deployment. Slot second portion 972 includes a width W2, narrower than width W1 of first portion 971, necessary to fixedly couple push tube 960 to lead body 950 when tool 97 is pushed, per arrow B, to engage sleeve within second portion 972. According to one embodiment of the present invention, tool 97 in the first position is used to facilitate gripping of push tube 960, to move push tube 960 distally, per arrow A (FIG. 9B), in order to deploy fixation segments 230; then, once fixation segments 230 are deployed to hold lead 900 at an implant site, tool 97 is moved into the second position, per arrow B, in order to hold fixation mechanism 920 in the deployed position while the implant procedure is being completed. With tool 97 in the second position, i.e. sleeve 961 engaged in second portion 972, to complete the lead implant procedure, a retention element, as previously described, may be engaged within one or more of grooves 964 in order to fixedly retain fixation mechanism 920 in the deployed position upon lead body 950. According to an exemplary embodiment of the present invention, tool 97 is formed from polycarbonate wherein width W1 is approximately 0.072 inch and width W2 is approximately is approximately 0.047 inch; sleeve 961 is formed from silicone rubber wherein an outer diameter of sleeve 961, where tool 97 is engaged, is approximately 0.095 inch and a corresponding inner diameter of sleeve 961 is approximately 0.051 inch; and an outer diameter of lead body 950 is approximately 0.044 inch. It should be noted that alternate embodiments of the present invention include holding tools employing other types of common clamping mechanisms known to those skilled in the art, for example a three jaw chuck type mechanism or a compression seal type mechanism, i.e. Touhy-Borst.

Finally, it should be noted that the features described in conjunction with FIGS. 9A-12 may be incorporated into any embodiments of the present invention which include a push tube segment extending from a proximal portion of a lead to a fixation segment that is positioned in proximity to a distal portion of the lead.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below, and, although described in the context of cardiac lead, embodiments of the present invention may be incorporated into a number of implantable medical devices, which require similar fixation in a body. It is therefore evident that the particular embodiments disclosed above may be altered or modified and all such variations are considered within the scope and spirit of the invention. Accordingly, the protection sought herein is as set forth in the claims below.

What is claimed is:

1. An implantable device, comprising:
   an elongate body including a proximal portion and a distal portion;
   a fixation mechanism formed about the body, extending from the proximal portion to the distal portion and comprising:
   a fixation segment positioned in proximity to a distal end of the fixation mechanism and including a deployable lobe,
   a push tube segment extending from the fixation segment proximally to a proximal end of the fixation mechanism, and
   an anchor fixedly coupling the fixation mechanism distal end to the body at a location spaced from a distal end of the body such that a portion of the distal portion of the body is located between the fixation mechanism distal end and the distal end of the body;
   a lubricious interface between the body and a portion of the push tube;
   wherein the distal portion of the body comprises a bend formed therein, wherein the bend is located between the fixation mechanism distal end and a distal end of the body, and wherein, when the portion of the body about which the fixation mechanism is formed is straight and a longitudinal axis is drawn through the center of that portion, the bend is such that a distal end of the body is deflected by a distance from the longitudinal axis that is greater than a height of the deployed lobe as measured from the longitudinal axis; and
   wherein the deployable lobe is deployed when the push tube segment is pushed distally.

2. The device of claim 1, wherein the lubricious interface comprises a hydrophilic layer fixed to an inner diameter of the push tube or to an outer diameter of the body.

3. The device of claim 1, wherein the lubricious interface comprises a coating of polyacrylamide bound to an inner surface of the push tube or an outer surface of the body.

4. The device of the claim 1, wherein the lubricious interface comprises a fluoropolymer layer fixed to an inner diameter of the push tube or to an outer diameter of the body.

5. The device of claim 1, wherein the deployable lobe includes a plurality of lobes positioned about a circumference of the body.

6. The device of claim 1, wherein the fixation segment includes a plurality of fixation segments positioned longitudinally along the body and each of the plurality of segments includes a deployable lobe.

7. The device of claim 6, wherein each deployable lobe includes a plurality of lobes formed by parallel slits through each of the plurality of fixation segments and positioned about a circumference of each of the plurality of fixation segments; and wherein the push tube compresses the plurality of fixation segments to deploy the pluralities of lobes.

8. The device of claim 6, wherein each deployable lobe includes a plurality of lobes formed by parallel slits through each of the plurality of fixation segments and positioned about a circumference of each of the plurality of fixation segments; and wherein the push tube compresses the plurality of fixation segments to deploy the pluralities of lobes.

9. The device of claim 1, wherein the deployable lobe includes an inner edge, the push tube includes a distal end portion engaging the inner edge, and the push tube forces the inner edge outward to deploy the lobe.

10. The device of claim 1, wherein the deployable lobe includes a plurality of lobes formed by parallel slits through the fixation segment and positioned about a circumference of the fixation segment and the push tube compresses the fixation segment to deploy the plurality of lobes.

11. The device of claim 1, wherein the device further comprises an electrode located at the distal tip of the lead body and a conductor that extends proximally from the electrode towards the proximal portion of the body.

12. The device of claim 11, wherein the conductor is located within the body and extends proximally through the body.

13. The device of claim 1, wherein the fixation segment comprises two deployable lobes and webbing material extending between the two deployable lobes.

* * * * *